United States Patent [19]

Böhner et al.

[11] Patent Number: 4,801,708
[45] Date of Patent: Jan. 31, 1989

[54] HERBICIDAL AND INSECTICIDAL TRIAZINONES

[75] Inventors: Beat Böhner, Binningen; Hans Tobler, Allschwil, both of Switzerland

[73] Assignee: Ciba-Geigy Corporation, Ardsley, N.Y.

[21] Appl. No.: 133,204

[22] Filed: Dec. 15, 1987

Related U.S. Application Data

[63] Continuation of Ser. No. 689,528, Jan. 7, 1985, abandoned.

[30] Foreign Application Priority Data

Jan. 11, 1984 [CH] Switzerland ............... 118/84

[51] Int. Cl.⁴ .......................................... C07D 253/06
[52] U.S. Cl. ...................................... 544/182
[58] Field of Search ........................... 544/182

[56] References Cited

U.S. PATENT DOCUMENTS

| | | | |
|---|---|---|---|
| 3,671,523 | 6/1972 | Westphal et al. | 260/248 |
| 3,905,801 | 9/1975 | Fawzi | 71/93 |
| 4,057,417 | 11/1977 | Dickore et al. | 544/182 |
| 4,346,220 | 8/1982 | Fawzi | 544/182 |
| 4,470,842 | 9/1984 | Kranz et al. | 544/182 |
| 4,544,744 | 10/1985 | Schmidt | 544/182 |
| 4,547,216 | 10/1985 | Bohner | 544/182 |

FOREIGN PATENT DOCUMENTS 0114783  8/1984  European Pat. Off. .

OTHER PUBLICATIONS

English language abstract of Japanese patent public. 58/180 492 Oct. 1983.

*Primary Examiner*—John M. Ford
*Attorney, Agent, or Firm*—Kevin T. Mansfield; Edward McC. Roberts

[57] ABSTRACT

The invention relates to 4-methylamino-1,2,4-triazin-5-one of the formula I

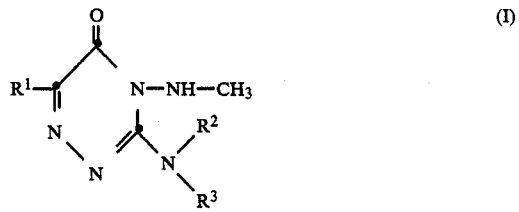

wherein
$R^1$ is $C_3$-$C_8$ cycloalkyl or $C_3$-$C_8$ cycloalkyl which is substituted by $C_1$-$C_4$alkyl; $C_3$-$C_8$halocycloalkyl, $C_3$-$C_8$alkyl, $C_3$-$C_8$haloalkyl, 2-furyl, 2-thienyl, phenyl, benzyl, or phenyl or benzyl each substituted by one or more members selected from the group consisting of halogen, $C_1$-$C_4$alkyl, $C_1$-$C_4$haloalkyl, $C_1$-$C_4$alkoxy or $C_1$-$C_4$haloalkoxy,
$R^2$ is hydrogen or methyl, and
$R^3$ is cyclopropyl, cyclopropylmethyl, $C_1$-$C_4$alkyl, $C_3$-$C_4$alkenyl or $C_3$-$C_4$alkynyl.

These compounds have selective herbicidal properties and are therefore pre-eminently suitable for controlling weeds in crops of useful plants, for example in cereals, maize, soybeans and sugar cane. They are also suitable for controlling harmful insects.

3 Claims, No Drawings

HERBICIDAL AND INSECTICIDAL TRIAZINONES

This application is a continuation of application Ser. No. 689,528, filed 1/7/85 abandoned.

The present invention relates to novel 4-methylamino-1,2,4-triazin-5-ones with herbicidal and insecticidal properties, to the preparation thereof, to compositions containing them, and to the use of said 4-methylamino-1,2,4-triazin-5-ones or of said compositions for controlling undesirable plant growth and harmful insects. The invention further relates to intermediates developed for producing the 4-methylamino-1,2,4-triazin-5-ones and to the preparation thereof.

A large number of herbicidally active 4-amino-1,2,4-triazinone derivatives which are substituted in the 3-position by mercapto, alkylthio, alkylamino or dialkylamino are known. However, only very sparse particulars are found in the literature on those triazinones in which the 4-amino group is mono- or disubstituted by methyl. Thus, for example, U.S. Pat. No. 3,671,523 discloses 3-methylthio-4-dimethylamino-6-tert-butyl-1,2,4-triazin-5-one and 3-mercapto-4-methylamino-6-phenyl-1,2,4-triazinon-5-one, while 3-isobutylthio-4-methylamino-6-(2-naphthyl)-1,2,4-triazin-5-one is known from U.S. Pat. No. 3,905,801. Further, Japanese patent publication No. 58/180 492 describes cyclic analogues of the above compounds, i.e. those compounds in which the 3-mercapto group and the 4-amino group are linked together to the ring structure, for example 3-(1,1-dimethylethyl)-4H-[1,3,4]thiadiazolo[2,3-c]-[1,2,4]-triazin-4-one. These known 1,2,4-triazinone derivatives which are described in the literature and are substituted in the 4-position by a methylamino or dimethylamino group have only a limited herbicidal activity which is insufficient for conditions of actual practice, and with some of these compounds no herbicidal activity at all is observed at customary rates of application. It must therefore be regarded as extremely surprising that the novel 3-alkylamino- or 3-dialkylamino-4-methylamino-1,2,4-triazinone derivatives which contain two directly vicinal exocyclic amino groups, of which that in the 4-position is monosubstituted by a methyl group and that in the 3-position is mono- or disubstituted by alkyl, are exceedingly potent herbicides, some of which are furthermore characterised by selective properties in important crops.

The novel 4-methylamino-1,2,4-triazin-5-ones are, in addition, most suitable for controlling harmful insects.

In particular, the compounds of formulae I and III are suitable for controlling insects of the orders Lepidoptera, Coleoptera (especially leaf-eating beetles and weevils), Homoptera (especially cicadas and aphids), Heteroptera, Diptera, Thysanoptera, Orthoptera, Anoplura, Siphonaptera, Mallophaga, Thysanura, Isoptera, Psocoptera and Hymenoptera.

The good insecticidal activity of the proposed compounds of the formulae I and III corresponds to a mortality of at least 50-60% of the above insect pests.

Although the field of triazinones has been intensively researched and the work done has resulted in a host of publications, 3-alkylamino- or 3-dialkylamino-4-methylamino-1,2,4-triazinones derivatives have so far not been described, with the exception of 3,4-bis(methylamino)-6-(1,1-dimethylethyl)-4H-1,2,4-triazin-5-one disclosed in European patent publication 114 783. This also applies to those compounds of the present invention in which the 3-amino group is substituted by other hydrocarbon radicals.

It has now been found that the novel 4-methylamino-1,2,4-triazin-5-ones are preeminently suitable for controlling undesirable plant growth, in particular for controlling weeds in crops of cultivated plants.

Specifically, the invention relates to novel 4-methylamino-1,2,4-triazin-5-ones of the formula I

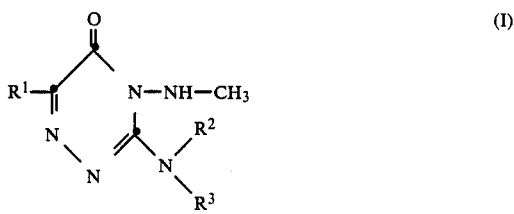

wherein
$R^1$ is $C_3$–$C_8$cycloalkyl or $C_3$–$C_8$cycloalkyl which is substituted by $C_1$–$C_4$alkyl; $C_3$–$C_8$halocycloalkyl, $C_3$–$C_8$alkyl, $C_3$–$C_8$haloalkyl, 2-furyl, 2-thienyl, phenyl, benzyl, or phenyl or benzyl each substituted by one or more members selected from the group consisting of halogen, $C_1$–$C_4$alkyl, $C_1$–$C_4$haloalkyl, $C_1$–$C_4$alkoxy or $C_1$–$C_4$haloalkoxy,
$R^2$ is hydrogen or methyl, and
$R^3$ is cyclopropyl, cyclopropylmethyl, $C_1$–$C_4$alkyl, $C_3$–$C_4$alkenyl or $C_3$–$C_4$alkynyl,
with the proviso that simultaneously $R^1$ may not be tert-butyl, $R^2$ may not be hydrogen and $R^3$ may not be methyl.

Depending on the indicated number of carbon atoms, alkyl denotes for example methyl, ethyl, n-propyl, isopropyl, the 4 butyl isomers as well as the isomers of pentyl, hexyl, heptyl or octyl. Alkyl is both the alkyl group itself and the moiety of another substituent such as alkoxy, haloalkyl or haloalkoxy. Alkenyl and alkynyl will be generally understood to mean allyl, methallyl, 2-butenyl, 3-butenyl, propargyl, 2-butynyl or 3-butynyl, with allyl and propargyl being preferred. Within the scope of this invention, cycloalkyl is cyclopropyl, cyclobutyl, cyclopentyl, cyclohexyl, cycloheptyl or cyclooctyl. Halogen as substituent of a larger radical is fluorine, chlorine, bromine or iodine, with fluorine and chlorine being preferred. Halogen-substituted radicals falling within the definition of $R^1$ can be mono- to perhalogenated. Thus, for example, halocycloalkyl comprises: 2-chlorocyclopropyl, 3-fluorocyclopentyl, 2-chlorocyclopentyl, 2,3-dichlorocyclopentyl, 2,3,4-trichlorocyclopentyl, 3,4-dichlorocyclopentyl, 3-fluorocyclopentyl, 3-bromocyclopentyl, 3-fluorocyclohexyl, 4-fluorocyclohexyl, 2-chlorocyclohexyl, 3-chlorocyclohexyl, 4-chlorocyclohexyl, 2,6-dichlorocyclohexyl, 2,4-dichlorocyclohexyl, 2,3,4,5,6-pentachlorocyclohexyl or 3,4,5-trichlorocyclohexyl; and substituted phenyl or benzyl comprises: 2-fluorophenyl, 2-chlorophenyl, 2-chloro-4-methoxyphenyl, 2-chloro-4-trifluoromethylphenyl, 2-chloro-4-trifluoromethoxyphenyl, 2,4-dichlorophenyl, 2,6-dichlorophenyl, 2,5-dichlorophenyl, 3,4-dichlorophenyl, 4-chlorophenyl, 4-trichloromethylphenyl, 4-trifluoromethylphenyl, 2-trifluoromethylphenyl, 4-trifluoromethoxyphenyl, 4-difluoromethoxyphenyl, 2-methoxyphenyl, 2-methylphenyl, 4-methylphenyl, 4-methoxyphenyl, 2,4-dimethoxyphenyl, 2-fluorobenzyl, 2-chlorobenzyl, 2,6-dichlorobenzyl or 3,4-dichlorobenzyl; and haloalkyl comprises: 3,3,3-trifluoropropyl, 1-chloromethylethyl, 1,1-dimethyl-2-chloroethyl, 1,1-dimethyl-2-fluoroethyl, 1,1-dimethyl-3-chloropropyl, 1-methyl-3-chloropropyl, 1-methyl-3-fluoropropyl or 2,3-dichloro-2-methylpropyl.

On account of their advantageous biological properties, those compounds of formula I are preferred wherein either (a) $R^1$ is a branched $C_3$–$C_6$alkyl group or a branched $C_3$–$C_6$haloalkyl group, or (b) $R^2$ is hydrogen or (c) $R^3$ is $C_1$–$C_4$alkyl, with the proviso that simultaneously $R^1$ may not be tert-butyl, $R^2$ may not be hydrogen and $R^3$ may not be methyl.

Within subgroup (a), preferred compounds are those in which $R^1$ is a branched $C_3$–$C_6$alkyl group; and within subgroup (c), preferred compounds are those wherein $R^3$ is methyl.

Further preferred subgroups comprise those compounds wherein $R^1$ is branched $C_3$–$C_6$alkyl or branched $C_3$–$C_6$haloalkyl, $R^2$ is hydrogen or methyl, and $R^3$ is $C_1$–$C_4$alkyl; or, in particular, those compounds wherein $R^1$ is branched $C_3$–$C_6$alkyl, $R^2$ is hydrogen and $R^3$ is methyl; and the same proviso as above applies.

Further preferred compounds are those wherein $R^1$ is phenyl or phenyl which is substituted by one or more members selected from the group consisting of halogen, $C_1$–$C_4$alkyl, $C_1$–$C_4$haloalkyl, $C_1$–$C_4$alkoxy or $C_1$–$C_4$haloalkoxy.

Preferred individual compounds of formula I are:

3,4-bis(methylamino)-6-isopropyl-4H-1,2,4-triazin-5-one, 3-dimethylamino-4-methylamino-6-(1,1-dimethylethyl)-4H-1,2,4-triazin-5-one, 3,4-bis(methylamino)-6-(1-methylpropyl)-4H-1,2,4-triazin-5-one, 3,4-bis(methylamino)-6-phenyl-4H-1,2,4-triazin-5-one and 3,4-bis(methylamino)-6-(2-fluorophenyl)-4H-1,2,4-triazin-5-one.

The compounds of formula I can be prepared by the processes described hereinafter.

Thus, for example, the compounds of formula I are obtained by (a) converting a 4-amino-4H-1,2,4-triazin-5-one of formula II

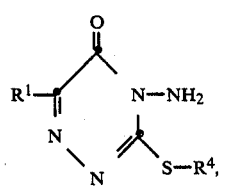
(II)

wherein $R^1$ is as defined for formula I and $R^4$ is methyl or ethyl, into a 4-methylamino-4H-1,2,4-triazin-5-one of formula III

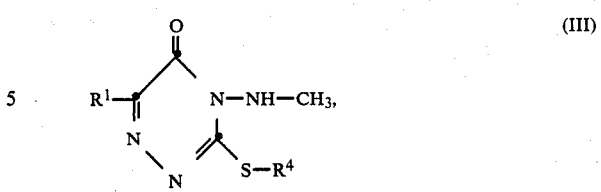
(III)

with a methylating agent, and reacting said compound of formula III, at elevated temperature, with an amine of formula IV $$H—NR^2R^3 \qquad (IV)$$

wherein $R^2$ and $R^3$ are as defined for formula I, with the proviso that, if $R^1$ is tert-butyl, simultaneously $R^2$ may not be hydrogen and $R^3$ may not be methyl or (b) reacting a 3,4-diamino-4H-1,2,4-triazin-5-one of formula V

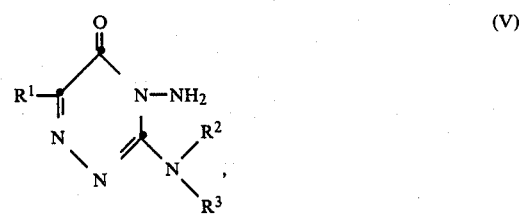
(V)

wherein $R^1$, $R^2$ and $R^3$ are as defined for formula I, with a methylating agent, with the proviso that, if $R^1$ is tert-butyl, simultaneously $R^2$ may not be hydrogen and $R^3$ may not be methyl.

In this process, the methylating steps (II→III and V→I) are conveniently carried out with a methyl halide, preferably methyl bromide or methyl iodide, or with dimethyl sulfate, in the presence of a phase transfer catalyst in a two-phase system. It is advantageous to perform the reaction in the presence of an organic water-immiscible solvent, an aqueous solution of a strong base and of a phase transfer catalyst; and it is particularly advantageous to add the amine of formula II or V to the mixture of the organic solvent and the strong base, and to add dimethyl sulfate, or preferably a methyl halide, and a phase transfer catalyst, preferably a quaternary ammonium salt or ammonium hydroxide or a phosphonium salt, to this mixture. Suitable strong bases are for example alkali metal hydroxides such as sodium or potassium hydroxide, or alkali metal carbonates or alkaline earth metal carbonates. Suitable methyl halides are for example methyl chloride, methyl bromide and, in particular, methyl iodide. Preferred ammonium salts or ammonium hydroxides are those selected from the group consisting of benzyltrialkylammonium or tetraalkylammonium hydroxides, bisulfites or halides, in which the alkyl moieties preferably contain from 1 to 4 carbon atoms, and are for example benzyltriethylammonium chloride, tetra-n-butylammonium hydroxide and benzyltrimethylammonium chloride. A tetraalkylammonium halide is particularly suitable, with tetra-n-butylammonium bromide being preferred. Examples of phosphonium salts are tributylhexadecylphosphonium bromide, ethyltriphenylphosphonium bromide, tetraphenylphosphonium chloride, benzyltriphenylphosphonium iodide, triphenyl n-propylphosphonium bromide and tetrabutylphosphonium chloride.

The methylation reaction can be carried out within a wide temperature range, with the range from 10° to 40° C. being particularly advantageous, and the most preferred range being from 20° to 25° C.

The reaction is conveniently carried out in the presence of a solvent or diluent. Examples of suitable solvents and diluents are aliphatic and aromatic hydrocarbons such as benzene, toluene, xylenes, petroleum ether, cyclohexane, n-hexane; halogenated hydrocarbons such as chlorobenzene, methylene chloride, ethylene chloride, chloroform, carbon tetrachloride, tetrachloroethylene; ethers and ethereal compounds such as dialkyl ethers, for example diethyl ether, diisopropyl ether; or mixtures of such solvents.

The amination step (III→I) is conveniently carried out at elevated temperature, preferably in the range from 100° to 200° C., most preferably from 140° to 160° C. It is advantageous to conduct this reaction in one of the inert solvents or mixtures of solvents employed for the methylation reaction.

The methyl or ethyl mercaptan formed in this reaction can be readily removed from the reaction mixture in known manner, for example by introducing into sodium hypochlorite.

With the exception of 3-methylthio-4-methylamino-6-tert-butyl-4,5-dihydro-1,2,4-triazin-5-one, which is known from Z. Naturforsch. 31b, 1122-1126 (1976), the intermediates of formula III are novel and have been specially developed for synthesizing the final products. Accordingly, they constitute an object of the invention.

The intermediates of formula III also have herbicidal properties. The use of these compounds as herbicides is therefore a further object of the invention.

The starting materials of formulae II, IV and V are known and some are commercially available.

The compounds of formula I can also be prepared by condensing an α-ketocarboxylic acid derivative of formula VI

R¹—CO—A     (VI), wherein R¹ is as defined for formula I and A is a member selected from —COOH, —COO—C₁-C₄alkyl, —COS—C₁-C₄alkyl, —CONH₂, —CONH—C₁-C₄—alkyl or CONH—CO—C₁-C₄alkyl, with a guanidine derivative of formula VII

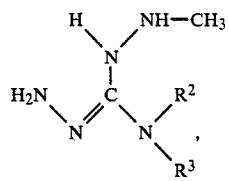

wherein R² and R³ are as defined for formula I.

3,4-Bis(methylamino)-6-(1,1-dimethylethyl)-4H-1,2,4-triazin-5-one, which is excluded under formula I, can also be prepared by this novel process.

The condensation reaction (VI+VII→I) is advantageously carried out in the presence of a catalytic amount of an organic or inorganic acid such as hydrochloric acid, sulfuric acid, methanesulfonic acid, toluenesulfonic acid, benzoic acid, acetic acid, trifluoroacetic acid or hydrobromic acid. Instead of a further addition of acid, the direct use of an acid addition salt of the guanidine derivative of formula VII, for example a hydrohalide such as the hydrochloride or hydroiodide, can also be advantageous. The reaction temperature is generally in the range from 20° to 150° C. If an activated carboxylic acid derivative of formula VI, for example an acylated carboxamide, is used as reactant, then it is possible to keep the reaction temperature low, e.g. at 20° C. Higher temperatures are normally necessary for the reaction of free α-ketocarboxylic acid groups. Preferably a temperature in the range from 50° to 90° C. is chosen. It is also advantageous to use an inert solvent in the condensation reaction. Examples of such solvents are water, an alcohol such as methanol, ethanol, ethylene glycol, propanol, isopropanol or butanol, or a water-soluble ether such as tetrahydrofuran, dioxan, ethylene glycol dimethyl ether or diethylene glycol dimethyl ether, or a mixture of such solvents.

The α-ketocarboxylic acid derivatives of formula VI are known and are either commercially available or can be prepared by methods analogous to known ones.

The guanidine derivatives of formula VII are novel and have been specially developed for synthesising the compounds of formula I. Together with their acid addition salts they therefore constitute a further object of the invention.

The preparation of the novel guanidine derivatives of formula VII can be carried out in accordance with the following scheme 1:

Scheme 1

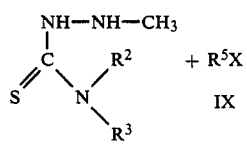

Scheme 1

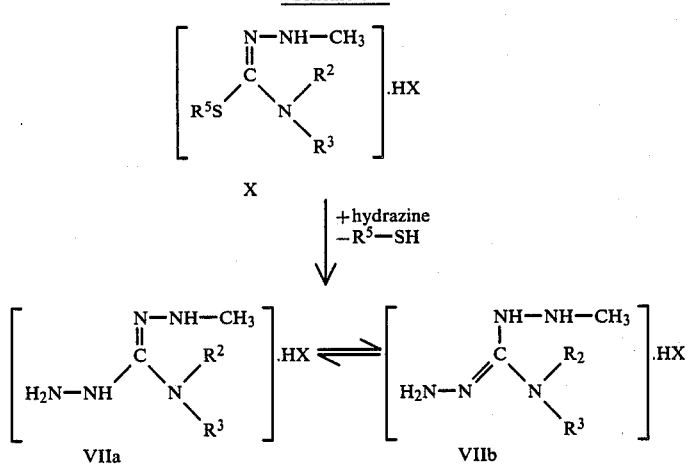

In scheme 1, $R^2$ and $R^3$ are as defined for formula I, X is the radical of an inorganic or strong organic acid, and $R^5$ is $C_1$-$C_4$alkyl, preferably methyl.

In accordance with the above scheme 1 for the preparation of the novel guanidine derivatives of formula VII, a thiosemicarbazide of formula VIII is first reacted with an alkylating agent of formula IX and the salt-like intermediate of formula X is converted with hydrazine into the guanidine derivative of formula VII, which is initially obtained in the form of the tautomeric acid addition salts of formulae VIIa and VIIb. If desired, the free compounds of formula VII can be obtained therefrom by treatment with a base. However, this liberation step is not necessary for the reaction of the guanidine derivatives of formula VII to give the compounds of formula I, and indeed for technical reasons it is advantageous to use the acid addition salt itself in the condensation reaction (VII+VI→I).

Examples of strong acids which are able to afford the radicals X contained in the alkylating agents $R^5X$ are hydrochloric acid, hydrobromic acid, hydriodic acid, sulfuric acid, methanesulfonic acid or trifluoromethanesulfonic acid.

The starting materials of formulae VIII and IX are known and most of the alkylating agents of formula IX are commercially available.

Finally, the compounds of the subformula Ia

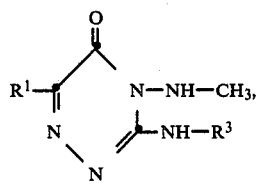 (Ia)

wherein $R^1$ and $R^3$ are as defined for formula I, can also be prepared from the suitable 4-amino-4H-1,2,4-triazin-5-ones of formula XI by selective monomethylation of the 4-amino group according to the following scheme 2:

Scheme 2

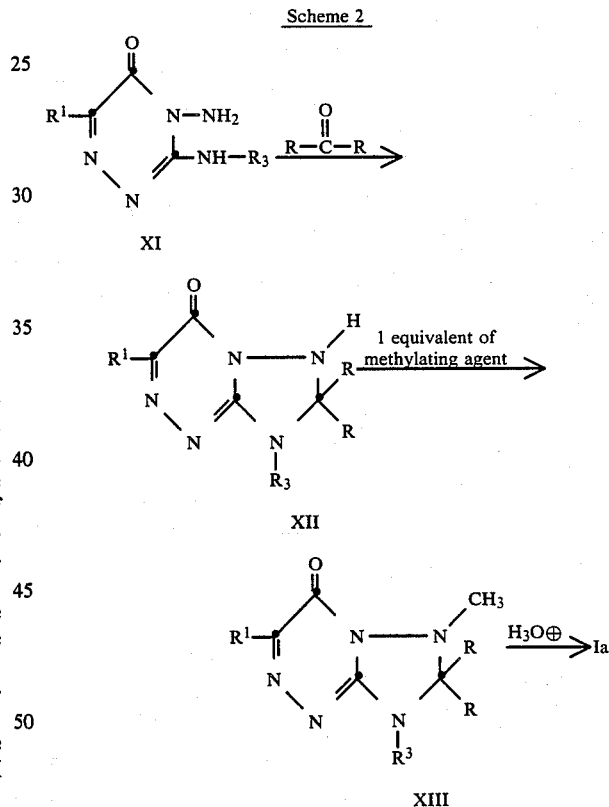

In scheme 2, $R^2$ and $R^3$ are as defined for formula I. R is $C_1$-$C_4$alkyl or the formula R—CO—R is a carbocyclic ketone such as cyclopentanone or cyclohexanone. The preferred ketone, however, is acetone or 2-butanone. The methylating agent is preferably a commercially available compound such as dimethyl sulfate, methyl chloride, methyl bromide or methyl iodide. Depending on the nature of the methylating agent employed, it may be convenient to carry out the reaction (XII→XIII) under pressure (0 to 20 bar).

In accordance with scheme 2, the 4-amino-4H-1,2,4-triazin-5-one of formula XI known from the literature is first converted with a ketone into the bicyclic structure of formula XII and then monomethylated (formula XIII). Finally, the ketone introduced as protecting group is removed by acid hydrolysis, affording the compound of formula Ia which is characterised by two secondary amino functions.

In a variant of this process (XI→Ia), the bis(methylamino)triazinones of the subformula Ib

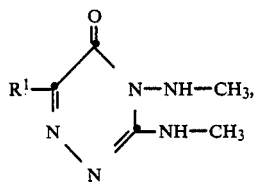

wherein $R^1$ is as defined for formula I, are obtained from the corresponding 3,4-diamino-4H-1,2,4-triazin-5-ones of formula XIV in accordance with scheme 3:

Scheme 3

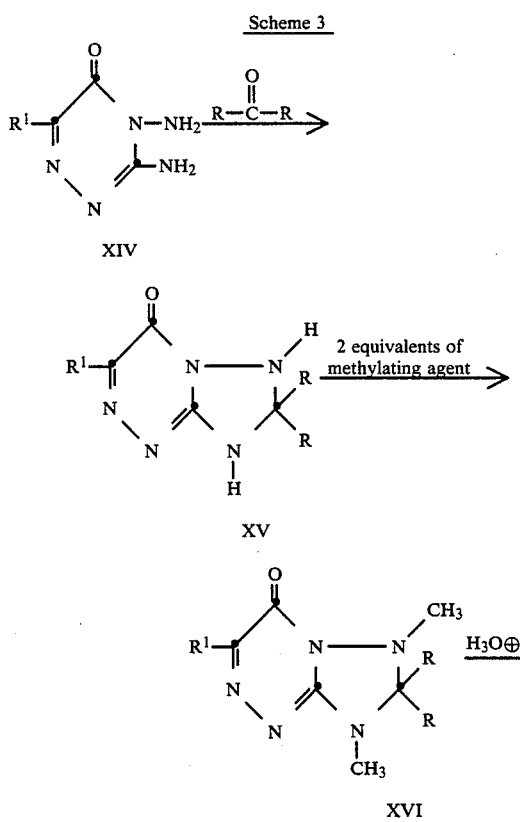

The reaction sequence in scheme 3 (XVI→Ib) is carried out in similar manner to scheme 2.

The starting compounds of formulae XI and XIV are either known from the literature or they can be prepared by procedures analogous to known ones.

For application as herbicides or insecticides, the compounds of formulae I and III are used in unmodified form or, preferably, together with the adjuvants conventionally employed in the art of formulation, and are therefore formulated in known manner to emulsifiable concentrates, coatable pastes, directly sprayable or dilutable solutions, dilute emulsions, wettable powders, soluble powders, dusts, granulates, and also encapsulations in e.g. polymer substances. As with the nature of the compositions, the methods of application, such as spraying, atomising, dusting, scattering, coating or pouring, are chosen in accordance with the intended objectives and the prevailing circumstances.

The formulations, i.e. the compositions or preparations containing the compound (active ingredient) of the formula I or III and, where appropriate, a solid or liquid adjuvant, are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol monomethyl or monoethyl ether, ketones such as cyclohexanone, strongly polar solvents such as N-methyl-2-pyrrolidone, dimethylsulfoxide or dimethylformamide, as well as vegetable oils or epoxidised vegatable oils such as epoxidised coconut oil or soybean oil; or water.

The solid carriers used e.g. for dusts and dispersible powders, are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are materials such as calcite or sand. In addition, a great number of pregranulated materials of inorganic or organic nature can be used, e.g. especially dolomite or pulverised plant residues.

Suitable surface-active compounds are nonionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids ($C_{10}$-$C_{22}$), e.g. the sodium or potassium salts of oleic or stearic acid, or of natural fatty acid mixtures which can be obtained e.g. from coconut oil or tallow oil. Mention may also be made of fatty acid methyltaurin salts.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and contain a $C_8$-$C_{22}$alkyl radical which also includes the alkyl moiety of acyl radicals, e.g. the sodium or calcium salt of lignosulfonic acid, of dodecylsulfate or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a naphthalenesulfonic acid/formaldehyde condensation product. Also suitable are corresponding phosphates, e.g. salts of the phosphoric acid ester of an adduct of p-nonylphenol with 4 to 14 moles of ethylene oxide, or phospholipids.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediamine polypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxypolyethoxyethanol. Fatty acid esters of polyoxyethylene sorbitan, such as polyoxyethylene sorbitan trioleate, are also suitable non-ionic surfactants.

Cationic surfactants are preferably quaternary ammonium salts which contain, as N-substituent, at least one $C_8$–$C_{22}$alkyl radical and, as further substituents, unsubstituted or halogenated alkyl, benzyl or hydroxy-lower alkyl radicals. The salts are preferably in the form of halides, methylsulfates or ethylsulfates, e.g. stearyltrimethylammonium chloride or benzyldi(2-chloroethyl)ethylammonium bromide.

The surfactants customarily employed in the art of formulation are described e.g. in "McCutcheon's Detergents and Emulsifiers Annual", MC Publishing Corp., Ridgewood, N.J., 1981; H. Stache, "Tensid-Taschenbuch", 2. Aufl., C. Hanser Verlag, Munich/Vienna, 1981; M. and J. Ash, "Encyclopedia of Surfactants", Vol. I–III, Chemical Publishing Co., New York, 1980–1981.

The agrochemical compositions usually contain 0.1 to 99%, preferably 0.1 to 95%, of active ingredient, 99.9 to 1%, preferably 99.8 to 5%, of a solid or liquid adjuvant, and 0 to 25%, preferably 0.1 to 25%, of a surfactant.

Whereas commercial products are preferably formulated as concentrates, the end user will normally employ dilute formulations.

The compositions may also contain further ingredients such as stabilisers, antifoams, viscosity regulators, binders, tackifiers as well as fertilisers or other active ingredients in order to obtain special effects.

The compounds of formulae I and III have pronounced herbicidal activity. They are suitable for controlling both monocot and dicot weeds pre- and post-emergence.

The compounds of I and III, or compositions containing them, can be used with particular advantage for selectively controlling weeds in crops of useful plants, for example in crops of cereals, maize, soybeans and, in particular, sugar cane. When these compounds are used in sugar cane, an appreciable increase in the sugar content can result.

The rates of application in which the novel 4-methylamino-1,2,4-triazin-5-ones are to be used depend on the respective conditions such as, in particular, the plant growth, the nature of the soil, the weather conditions and the time of application. Rates of application of 30 to 2000 g/hectare normally prove suitable.

PREPARATORY EXAMPLES

Example P1

3,4-Bis(methylamino)-6-phenyl-4H-1,2,4-triazin-5-one (compound 1.11)

(a) 4-Methylamino-3-methylthio-6-phenyl-4H-1,2,4-triazin-5-one (compound 2.5)

A two-phase mixture of 35.1 g (0.15 mole) of 4-amino-3-methylthio-6-phenyl-4H-1,2,4-triazin-5-one, 24.4 ml (0.375 mole) of methyl iodide, 5 g of tetrabutylammonium bromide, 200 ml of toluene and 60 ml of a 50% solution of sodium hydroxide is efficiently stirred for 2 hours, the temperature rising from 20° to 40° C. The organic phase is separated and filtered over silica gel. Evaporation of the filtrate yields 25.1 g (67.5% of theory) of 4-methylamino-3-methylthio-6-phenyl-4H-1,2,4-triazin-5-one which melts at 119°–120° C.

(b) 10.0 g (0.04 mole) of 4-methylamino-3-methylthio-6-phenyl-4H-1,2,4-triazin-5-one, 1.6 g (0.05 mole) of methylamine and 50 ml of isopropanol are heated for 4 hours in a bomb tube to 155° C. The resultant clear orange solution is concentrated by evaporation and the residue is chromatographed through silica gel eluted with a 95:5 mixture of methylene chloride/ether. The eluate is concentrated by evaporation and the residue is washed with petroleum ether, affording 8.1 g (88% of theory) of 3,4-bis(methylamino)-6-phenyl-4H-1,2,4-triazin-5-one with a melting point of 150°–151° C.

Example P2

3,4-Bis(methylamino)-6-(3-fluorophenyl)-4H-1,2,4-triazin-5-one (compound 1.5)

(a) 1,2-Dimethyl-3-methylamino-isothiourea hydroiodide

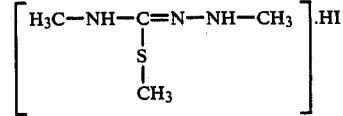

85.8 g (0.712 mole) of 1,4-dimethylthiosemicarbazide ($H_3C$—NH—CS—NH—NH—$CH_3$), 103 g of methyl iodide and 360 ml of absolute ethanol are heated for 7 hours in an autoclave to a temperature in the range from 90°–95° C. under a maximum pressure of 1 bar. The suspension obtained after cooling is concentrated by evaporation and the residue is washed with a small amount of cold ethanol and with diethyl ether, affording 161.7 g (86% of theory) of 1,2-dimethyl-3-methylamino-isothiourea hydroiodide as colourless crystalline solid. Melting point: 121°–122° C.

(b) 1-Amino-2-methyl-3-methylaminoguanidine hydroiodide 161.7 g (0.6195 mole) of 1,2-dimethyl-3-methylamino-isothiourea hydroiodide are dissolved in 850 ml of ethanol. After the solution has been heated to 60° C., 21.5 g of hydrazine in 30 ml of ethanol are slowly added dropwise, giving rise to evolution of methyl mercaptan. To bring the reaction to completion, the mixture is heated for 1½ hours to reflux. When evolution of gas has ceased, the mixture is cooled and concentrated by evaporation. The crystalline residue is washed with diethyl ether, affording 144.9 g (95.5% of theory) of 1-amino-2-methyl-3-methylaminoguanidine hydroiodide with a melting point of 175°–177° C.

(c) 3.8 g (0.02 mole) of 3-fluorophenylglyoxylic acid in 10 ml of ethanol are slowly added dropwise to a solution of 5.4 g (0.022 mole) of 1-amino-2-methyl-3-methylaminoguanidine hydroiodide in 55 ml of 2N hydrochloric acid. The temperature rises from 20° to 30° C. during this addition and a pale yellow precipitate forms. This mixture is stirred for 2 hours to a temperature in the range from 60° to 70° C., whereupon a clear yellow orange solution forms. After cooling, this solution is neutralised with an aqueous solution of sodium hydroxide. The precipitate is then isolated, washed with water and dried at 70° C., affording 4.3 g (76% of theory) of 3,4-bis(methylamino)-6-(3-fluorophenyl)-4H-1,2,4-triazin-5-one with a melting point of 173°–174° C.

Example P3

3,4-Bis(methylamino)-6-(1,1-dimethylethyl)-4H-1,2,4-triazin-5-one (a) 3-(1,1-Dimethylethyl)-7,7,8-trimethyl-5,6,7,8-tetrahydro-5H-[1,2,4]triazolo[5,1-c][1,2,4]triazin-4-one

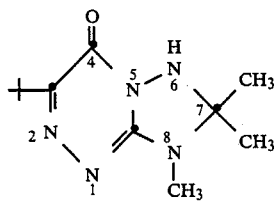

19.7 g (0.082 mole) of 4-amino-3-methylamino-6-(1,1-dimethylethyl)-4H-1,2,4-triazin-5-one, 50 ml of acetone and 50 ml of glacial acetic acid are heated for 1 hour to reflux. The reaction mixture is then concentrated by evaporation and the residue is crystallised from a mixture of ether/petroleum ether, affording 21.6 g (91% of theory) of 3-(1,1-dimethylethyl)-7,7,8-trimethyl-5,6,7,8-tetrahydro-5H-[1,2,4]triazolo[5,1-c][1,2,4]triazin-4-one with a melting point of 165°–168° C.

(b) 3-(1,1-Dimethylethyl)-6,7,7,8-tetramethyl-5,6,7,8-tetrahydro-5H-[1,2,4]triazolo[5,1-c][1,2,4]triazin-4-one A two-phase mixture of 11.0 g (0.046 mole) of 3-(1,1-dimethylethyl)-7,7,8-trimethyl-5,6,7,8-tetrahydro-5H-[1,2,4]triazolo[5,1-c][1,2,4]triazin-4-one, 3.0 g of tetrabutylammonium bromide, 12.5 ml (0.2 mole) of methyl iodide, 25 ml of toluene and 20 ml of 50% sodium hydroxide solution is efficiently stirred for 1 hour, the temperature rising from 20° to 40° C. To bring the reaction to completion, the mixture is warmed to 50° C. and stirred for another hour. The organic phase is separated and concentrated by evaporation. The residue is crystallized from ethyl acetate, affording 7.4 g (63.8% of theory) of 3-(1,1-dimethylethyl)-6,7,7,8-tetramethyl-5,6,7,8-tetrahydro-5H-[1,2,4]triazolo[5,1-c][1,2,4]triazin-4-one with a melting point of 120°–121° C.

(c) 2.5 g (0.01 mole) of 3-(1,1-dimethylethyl)-6,7,7,8-tetramethyl-5,6,7,8-tetrahydro-5H-[1,2,4]triazolo[5,1-c][1,2,4]triazin-4-one are dissolved in 10 ml of isopropanol and to this solution is added 0.15 g of p-toluenesulfonic acid. Then 0.72 ml of water and 10 ml of ethylene glycol monomethyl ether are added at 60° C. The reaction mixture is then heated on an oil bath to 155° C. After 10 minutes a thin-layer chromatogram shows that no more starting material is present. The reaction mixture is evaporated to dryness and the oily residue is dissolved in methylene chloride and the solution is filtered over silica gel. The filtrate is concentrated by evaporation and the residue is crystallised from ether/petroleum ether, affording 2.0 g (95.2% of theory) of 3,4-bis(methylamino)-6-(1,1-dimethylethyl)-4H-1,2,4-triazin-5-one with a melting point of 170°–171° C.

Example P4

3,4-Bis(methylamino)-6-(1,1-dimethylethyl)-4H-1,2,4-triazin-5-one (a) 3,4- Diamino-6-(1,1-dimethylethyl)-4H-1,2,4-triazin-5-one 3.8 g (0.03 mole) of diaminoguanidine hydrochloride are dissolved in 35 ml of water. To this solution are added 5.1 g (0.03 mole) of N-acetyl-3,3,3-trimethylpyruvamide and the reaction mixture is heated for 15 minutes to 90° C. The reaction mixture is filtered and the filtrate is neutralised by addition of crystalline sodium bicarbonate. At pH 7, 3.6 g (66.7% of theory) of 3,4-diamino-6-(1,1-dimethylethyl)-4H-1,2,4-triazin-5-one precipitate in the form of a yellowish crystalline solid with a melting point of 223°–224° C.

(b) 3-(1,1-Dimethylethyl)-7,7-dimethyl-5,6,7-tetrahydro-5H-[1,2,4]triazolo[5,1-c][1,2,4]triazin-4-one 7.0 g (0.0382 mole) of 3,4-diamino-6-(1,1-dimethylethyl)-4H-1,2,4-triazin-5-one are refluxed in 150 ml of acetone. A clear solution forms after 1 hour. To this solution are added 4 g of solid sodium hydroxide and the mixture is heated at 50° C. and stirred for about 30 minutes. Afterwards a thin-layer chromatogram shows that no more starting material is present. The batch is cooled and then 10.5 g of yellow precipitate are isolated by filtration. During filtration care is taken that solid sodium hydroxide remains in the reaction vessel. The isolated yellow product is dissolved in 50 ml of water and the solution is neutralised with 36% hydrochloric acid, whereupon the clear yellow solution becomes colourless. A colourless precipitate falls out of the solution at pH 7. this crystalline product is isolated, affording 5.0 g (59.5% of theory) of 3-(1,1-diethylthyl)-7,7-dimethyl-5,6,7,8-tetrahydro-5H-[1,2,4]triazolo[5,1-c][1,2,4]triazin-4-one with a melting point of 170°–172° C.

(c) 3-(1,1-Dimethylethyl)-6,7,7,8-tetramethyl-5,6,7,8-tetrahydro-5H-[1,2,4]triazolo[5,1-c][1,2,4]triazin-4-one A two-phase mixture of 4.9 g (0.022 mole) of 3-(1,1-dimethylethyl)-7,7-dimethyl-5,6,7,8-tetrahydro-5H-[1,2,4]triazolo[5,1-c][1,2,4]triazin-4-one, 1.5 g of tetrabutylammonium bromide, 6.2 ml (0.1 mole) of methyl iodide, 12 ml of toluene and 10 ml of 50% sodium hydroxide solution is efficiently stirred for 1 hour, the temperature of the reaction mixture rising from 20° to 30° C. The mixture is then heated for another 15 minutes to 40° C. and extracted with ethyl acetate. The organic phase is concentrated by evaporation, affording 5.9 g of an orange red oil which contains 12.7% of an isomer. This isomer is removed by column chromatography. The main fraction is concentrated by evaporation and the residue is crystallised from ether/petroleum ether, affording pure 3-(1,1-dimethylethyl)-6,7,7,8-tetramethyl-5,6,7,8-tetrahydro-5H-[1,2,4]triazolo[5,1-c][1,2,4]triazin-4-one with a melting point of 120°–121° C.

(d) 1.25 g (0.005 mole) of 3-(1,1-dimethylethyl)-6,7,7,8-tetramethyl-5,6,7,8-tetrahydro-5H-[1,2,4]triazolo[5,1-c][1,2,4]triazin-4-one are suspended in 10 ml of 1N hydrochloric acid and heated, with stirring, to 90° C. After 15 minutes a thin-layer chromatogram shows that no more starting material is present in the mixture. After cooling, the mixture is neutralised with 1N sodium hydroxide solution, whereupon 0.5 g (50% of theory) of 3,4-bis(methylamino)-6-(1,1-(dimethylethyl)-4H-1,2,4-triazin-5-one with a melting point of 170°–172° C. are obtained.

The intermediates and final products listed in the following tables, together with the compounds of formulae I and III of the above Examples, are obtained in analogous manner.

TABLE 1

| Compound | $R^1$ | $R^2$ | $R^3$ | Physical data |
|---|---|---|---|---|
| 1.1 | $C_4H_9$—t | $CH_3$ | $CH_3$ | m.p. 69–70° C. |
| 1.2 | $C_4H_9$—s | H | $CH_3$ | m.p. 93–94° C. |
| 1.3 | $C_4H_9$—t | H | $C_3H_7$—n | m.p. 43–47° C. |
| 1.4 | $C_4H_9$—t | H | $C_3H_7$—i | m.p. 72–74° C. |
| 1.5 | 3-F—$C_6H_4$— | H | $CH_3$ | m.p. 173–174° C. |
| 1.6 | $C_4H_9$—t | H | $CH_2CH=CH_2$ | oil |
| 1.7 | $C_4H_9$—t | H | $C_3H_5$—cycl. | m.p. 165–166° C. |
| 1.8 | $C_3H_7$—i | H | $CH_3$ | m.p. 177–118° C. |
| 1.9 | $C_6H_{11}$—cycl. | H | $CH_3$ | m.p. 121–122° C. |
| 1.10 | $C_4H_9$—t | H | $C_4H_9$—n | m.p. 79–80° C. |
| 1.11 | $C_6H_5$— | H | $CH_3$ | m.p. 150–151° C. |
| 1.12 | 3-Cl—$C_6H_4$— | H | $CH_3$ | m.p. 136–138° C. |
| 1.13 | 3-$CF_3$—$C_6H_4$ | H | $CH_3$ | viscous |
| 1.14 | 3-$CH_3$—$C_6H_4$— | H | $CH_3$ | m.p. 123–125° C. |
| 1.15 | 4-Cl—$C_6H_4$— | H | $CH_3$ | m.p. 168–169° C. |
| 1.16 | 4-$CF_3$—$C_6H_4$ | H | $CH_3$ | m.p. 191–192° C. |
| 1.17 | $ClCH_2$—$C(CH_3)_2$— | H | $CH_3$ | m.p. 110–111° C. |
| 1.18 | $ClCH_2$—$C(CH_3)_2$— | $CH_3$ | $CH_3$ | |
| 1.19 | 3-$CF_3$—$C_6H_4$— | $CH_3$ | $CH_3$ | m.p. 132–133° C. |
| 1.20 | 3-Cl—$C_6H_4$— | $CH_3$ | $CH_3$ | m.p. 99–101° C. |
| 1.21 | 3-F—$C_6H_4$— | $CH_3$ | $CH_3$ | m.p. 89–90° C. |
| 1.22 | $C_6H_5$— | $CH_3$ | $CH_3$ | m.p. 88–89° C. |
| 1.23 | $C_6H_{11}$—cycl. | $CH_3$ | $CH_3$ | |
| 1.24 | $C_3H_7$—i | $CH_3$ | $CH_3$ | $n_D^{22} = 1.5366$ |
| 1.25 | $C_4H_9$—s | $CH_3$ | $CH_3$ | $n_D^{22} = 1.5297$ |
| 1.26 | $C_3H_7$—$C(CH_3)_2$— | H | $CH_3$ | |
| 1.27 | $C_3H_7$—$C(CH_3)_2$— | $CH_3$ | $CH_3$ | |
| 1.28 | $(CH_3)_3C$—$CH_2$— | H | $CH_3$ | |
| 1.29 | $(CH_3)_3C$—$CH_2$— | $CH_3$ | $CH_3$ | m.p. 91–92° C. |
| 1.30 | 1-methylcyclopentyl | H | $CH_3$ | |
| 1.31 | 1-methylcyclopentyl | $CH_3$ | $CH_3$ | |
| 1.32 | 1-methylcyclohexyl | H | $CH_3$ | |
| 1.33 | 1-methylcyclohexyl | $CH_3$ | $CH_3$ | |
| 1.34 | 1-ethylcyclopentyl | H | $CH_3$ | |
| 1.35 | 1-ethylcyclopentyl | $CH_3$ | $CH_3$ | |
| 1.36 | 3-Br—$C_6H_4$— | H | $CH_3$ | m.p. 138–141° C. |
| 1.37 | $C_4H_9$—t | H | $C_2H_5$ | m.p. 126–127° C. |
| 1.38 | $C_6H_5$ | H | $C_2H_5$ | m.p. 133–134° C. |
| 1.39 | 2-thienyl | H | $CH_3$ | m.p. 190–191° C. |
| 1.40 | $(CH_3)_2CH$—$CH_2$— | H | $CH_3$ | m.p. 119–120° C. |
| 1.41 | 3-Br—$C_6H_4$ | $CH_3$ | $CH_3$ | m.p. 133–134° C. |
| 1.42 | 3-$CH_3$—$C_6H_4$ | $CH_3$ | $CH_3$ | m.p. 88–90° C. |
| 1.43 | 4-Cl—$C_6H_4$ | $CH_3$ | $CH_3$ | m.p. 118–120° C. |
| 1.44 | 2-F—$C_6H_4$ | H | $CH_3$ | m.p. 145–146° C. |
| 1.45 | 4-$CH_3$—$C_6H_4$ | $CH_3$ | $CH_3$ | m.p. 102–103° C. |
| 1.46 | 2-F—$C_6H_4$ | $CH_3$ | $CH_3$ | m.p. 79–81° C. |
| 1.47 | 2-$CH_3$—$C_6H_4$ | H | $CH_3$ | m.p. 120–122° C. |
| 1.48 | $(CH_3)_2CH$—$CH_2$— | $CH_3$ | $CH_3$ | $n_D^{22}$: 1.5316 |
| 1.49 | $(C_2H_5)_2CH$— | $CH_3$ | $CH_3$ | $n_D^{22}$: 1.5164 |
| 1.50 | 2-$CH_3$—$C_6H_4$ | $CH_3$ | $CH_3$ | m.p. 122–124° C. |
| 1.51 | 4-$CH_3$—$C_6H_4$ | H | $CH_3$ | m.p. 160–162° C. |
| 1.52 | $C_3H_7$—$CH(CH_3)$— | $CH_3$ | $CH_3$ | $n_D^{22}$: 1.5273 |
| 1.53 | 3-$CH_3$—$C_6H_4$—$CH_2$— | H | $CH_3$ | m.p. 96–98° C. |
| 1.54 | 2-F, 6-F—$C_6H_3$ | H | $CH_3$ | m.p. 193–195° C. |
| 1.55 | 2-F, 6-F—$C_6H_3$ | $CH_3$ | $CH_3$ | m.p. 113–115° C. |
| 1.56 | 2-Cl, 6-Cl—$C_6H_3$ | H | $CH_3$ | |
| 1.57 | 2-Cl, 6-Cl—$C_6H_3$ | $CH_3$ | $CH_3$ | |
| 1.58 | 2-$C_2H_5$—$C_6H_4$ | H | $CH_3$ | m.p. 70–74° C. |
| 1.59 | 2-$C_2H_5$—$C_6H_4$ | $CH_3$ | $CH_3$ | m.p. 80–82° C. |
| 1.60 | 2-$CH_3$, 6-$CH_3$—$C_6H_3$ | H | $CH_3$ | |
| 1.61 | 2-$CH_3$, 6-$CH_3$—$C_6H_3$ | $CH_3$ | $CH_3$ | |
| 1.62 | 2-$C_3H_7$—i-$C_6H_4$ | H | $CH_3$ | |

TABLE 1-continued

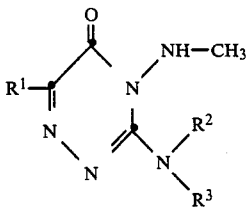

| Compound | R¹ | R² | R³ | Physical data |
|---|---|---|---|---|
| 1.63 | 2-$C_3H_7$—i-$C_6H_4$ | $CH_3$ | $CH_3$ | |
| 1.64 | 2-Cl—$C_6H_4$ | H | $CH_3$ | m.p. 120–122° C. |
| 1.65 | 2-Cl—$C_6H_4$ | $CH_3$ | $CH_3$ | |
| 1.66 | 3-Cl, 4-Cl—$C_6H_3$ | H | $CH_3$ | m.p. 207–209° C. |
| 1.67 | 2-Cl, 4-Cl—$C_6H_3$ | H | $CH_3$ | m.p. 178–180° C. |

TABLE 2

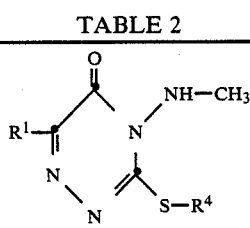

| Compound. | R¹ | R⁴ | Physical data |
|---|---|---|---|
| 2.1 | $C_4H_9$—s | $CH_3$ | oil, $n_D^{22}$ = 1.5598 |
| 2.2 | $C_6H_{11}$—cycl. | $CH_3$ | oil |
| 2.3 | $C_3H_7$—i | $CH_3$ | m.p. 79–80° C. |
| 2.4 | $C_4H_9$—i | $CH_3$ | m.p. 71–73° C. |
| 2.5 | $C_6H_5$ | $CH_3$ | m.p. 119–120° C. |
| 2.6 | 3-F—$C_6H_4$ | $CH_3$ | m.p. 173–175° C. |
| 2.7 | 4-Cl—$C_6H_4$ | $CH_3$ | m.p. 204–206° C. |
| 2.8 | 3-Cl—$C_6H_4$ | $CH_3$ | m.p. 195–197° C. |
| 2.9 | 3-Br—$C_6H_4$ | $CH_3$ | m.p. 204–205° C. |
| 2.10 | 3-$CH_3$—$C_6H_4$ | $CH_3$ | m.p. 154–156° C. |
| 2.11 | 3-$CF_3$—$C_6H_3$ | $CH_3$ | m.p. 170–172° C. |
| 2.12 | $C_6H_5$ | $C_2H_5$ | m.p. 125–126° C. |
| 2.13 | $C_6H_{11}$cycl. | $C_2H_5$ | $n_D^{23}$: 1.5574 |
| 2.14 | $C_4H_9$—t | $C_2H_5$ | m.p. 61–62° C. |
| 2.15 | $C_3H_7$—i | $C_2H_5$ | m.p. 71–72° C. |
| 2.16 | $C_4H_9$—s | $C_2H_5$ | $n_D^{23}$: 1.5466 |
| 2.17 | $(C_2H_5)_2CH$— | $C_2H_5$ | $n_D^{23}$: 1.5457 |
| 2.18 | 2-F—$C_6H_4$ | $CH_3$ | m.p. 96–98° C. |
| 2.19 | 4-$CH_3$—$C_6H_4$ | $CH_3$ | m.p. 165–166° C. |
| 2.20 | $(C_2H_5)_2CH$— | $CH_3$ | $n_D^{22}$: 1.5448 |
| 2.21 | 2-$CH_3$—$C_6H_4$ | $CH_3$ | m.p. 131–133,5° C. |
| 2.22 | $CH_3$—$CH_2CH_2$—CH—<br>\|<br>($CH_3$) | $CH_3$ | $n_D^{22}$: 1.5520 |
| 2.23 | 2-Furyl | $CH_3$ | m.p. 170–171° C. |
| 2.24 | $(CH_3)_3C$—$CH_2$— | $CH_3$ | m.p. 88–89° C. |
| 2.25 | 2-F, 6-F—$C_6H_3$ | $CH_3$ | m.p. 156–158° C. |
| 2.26 | 2-Cl, 6-Cl—$C_6H_3$ | $CH_3$ | |
| 2.27 | 2-$CH_3$, 6-$CH_3$—$C_6H_3$ | $CH_3$ | |
| 2.28 | 2-$C_2H_5$—$C_6H_4$ | $CH_3$ | m.p. 81–82° C. |
| 2.29 | 2-$C_3H_7$—i-$C_6H_4$ | $CH_3$ | |
| 2.30 | 2-Cl—$C_6H_4$ | $CH_3$ | |

Formulation Examples (throughout, percentages are by weight)

| F1. Wettable powders | (a) | (b) | (c) |
|---|---|---|---|
| compound of formula I or III | 25% | 50% | 75% |
| sodium lignosulfonate | 5% | 5% | — |
| sodium lauryl sulfate | 3% | — | 5% |
| sodium diisobutylnaphthalenesulfonate | — | 6% | 10% |
| octylphenol polyethylene glycol ether (7-8 moles of ethylene oxide) | — | 2% | — |
| highly dispersed silicic acid | 5% | 10% | 10% |
| kaolin | 62% | 27% | — |

The active ingredient is thoroughly mixed with the adjuvants and the mixture is thoroughly ground in a suitable mill, affording wettable powders which can be diluted with water to give suspensions of the desired concentration.

| F2. Emulsifiable concentrate | |
|---|---|
| compound of formula I or III | 10% |
| octylphenol polyethlene glycol ether (4-5 moles of ethylene oxide) | 3% |
| calcium dodecylbenzenesulfonate | 3% |
| castor oil polyglycol ether (35 moles of ethylene oxide) | 4% |
| dimethylformamide | 20% |
| cyclohexanone | 20% |
| xylene mixture | 40% |

Emulsions of any required concentration can be obtained from this concentrate by dilution with water.

| F3. Dusts | (a) | (b) |
|---|---|---|
| compound of formula I or III | 5% | 8% |
| talcum | 95% | — |
| kaolin | — | 92% |

Ready-for-use dusts are obtained by mixing the active ingredient with the carriers, and grinding the mixture in a suitable mill.

| F4. Extruder granulate | |
|---|---|
| compound of formula I or III | 10% |
| sodium lignosulfonate | 2% |
| carboxymethylcellulose | 1% |
| kaolin | 87% |

The active ingredient is mixed and ground with the adjuvants, and the mixture is subsequently moistened with water. The mixture is extruded and then dried to a stream of air.

| F5. Coated granulate | |
|---|---|
| compound of formula I or III | 3% |
| polyethylene glycol (mol. wt. 200) | 3% |

| F5. Coated granulate | |
|---|---|
| kaolin, granulated | 94% |

The finely ground active ingredient is uniformly applied, in a mixer, to the granulated kaolin moistened with polyethlene glycol. Non-dusty coated granulates are obtained in this manner.

| F6. Suspension concentrate | |
|---|---|
| compound of formula I or III | 40% |
| ethylene glycol | 10% |
| nonylphenol polyethylene glycol (15 moles of ethylene oxide) | 6% |
| sodium lignosulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient is intimately mixed with the adjuvants, giving a suspension concentrate from which suspensions of any desired concentration can be obtained by dilution with water.

Biological Examples

Example B1

Preemergence herbicidal action

In a greenhouse, directly after sowing the test plants in pots of 11 cm diameter, the surface of the soil is treated with an aqueous dispersion of a compound of formula I or III, obtained from a 25% wettable powder or a 25% emulsifiable concentrate. Concentrations of 4 kg/hectare are employed. The pots with the plants are then kept in the greenhouse at 20°–24° C. and 50–70% relative humidity. The test is evaluated after 3 weeks and the results are expressed in according with the following rating:

1 = plants have not germinated or have totally perished
2-3 = very pronounced activity
4-6 = average activity
7-8 = slight activity
9 = no activity (as untreated controls)

The results are as follows:

TABLE 3

Preemergence action
Rate of application: 4 kg of active ingredient/hectare

| Compound | Avena | Setaria | Sinapis | Stellaria |
|---|---|---|---|---|
| 1.1 | 1 | 1 | 1 | 1 |
| 1.2 | 1 | 1 | 1 | 2 |
| 1.3 | 2 | 1 | 1 | 2 |
| 1.4 | 1 | 1 | 1 | 2 |
| 1.5 | 2 | 1 | 1 | 2 |
| 1.6 | 1 | 1 | 1 | 1 |
| 1.7 | 2 | 1 | 1 | 1 |
| 1.8 | 1 | 1 | 1 | 2 |
| 1.9 | 2 | 1 | 1 | 1 |
| 1.11 | 1 | 1 | 1 | 2 |
| 1.12 | 1 | 1 | 1 | 2 |
| 1.13 | 1 | 1 | 1 | 1 |
| 1.14 | 1 | 1 | 1 | 2 |
| 1.15 | 2 | 1 | 1 | 1 |
| 1.16 | 2 | 1 | 1 | 1 |
| 1.17 | 2 | 1 | 1 | 1 |
| 1.19 | 1 | 1 | 1 | 1 |
| 1.20 | 2 | 1 | 1 | 2 |
| 1.21 | 1 | 1 | 1 | 1 |
| 1.22 | 1 | 1 | 1 | 1 |
| 1.24 | 1 | 1 | 1 | 1 |
| 1.25 | 1 | 1 | 1 | 1 |
| 1.36 | 2 | 1 | 1 | 1 |
| 1.37 | 2 | 1 | 1 | 2 |
| 1.38 | 1 | 1 | 1 | 1 |
| 1.39 | 1 | 1 | 1 | 1 |
| 1.40 | 1 | 1 | 1 | 1 |
| 1.41 | 1 | 2 | 1 | 1 |
| 1.42 | 1 | 1 | 1 | 1 |
| 1.43 | 2 | 1 | 1 | 2 |
| 1.44 | 1 | 1 | 1 | 1 |
| 1.45 | 1 | 1 | 1 | 4 |
| 1.46 | 1 | 1 | 1 | 1 |
| 1.47 | 1 | 1 | 1 | 1 |
| 1.48 | 1 | 1 | 1 | 1 |
| 1.49 | 1 | 1 | 1 | 1 |
| 1.50 | 1 | 1 | 1 | 1 |
| 1.51 | 1 | 1 | 1 | 1 |
| 2.1 | 1 | 1 | 1 | 2 |
| 2.2 | 2 | 1 | 1 | 1 |
| 2.3 | 1 | 1 | 1 | 2 |
| 2.4 | 2 | 1 | 1 | 2 |
| 2.5 | 2 | 1 | 1 | 1 |
| 2.6 | 1 | 1 | 1 | 1 |
| 2.10 | 1 | 1 | 1 | 1 |
| 2.11 | 1 | 7 | 2 | 2 |
| 2.12 | 8 | 6 | 9 | 6 |
| 2.13 | 1 | 1 | 1 | 1 |
| 2.14 | 8 | 1 | 2 | 5 |
| 2.16 | 2 | 1 | 1 | 1 |
| 2.17 | 2 | 3 | 2 | 1 |
| 2.18 | 1 | 1 | 1 | 1 |
| 2.19 | 5 | 4 | 1 | 1 |
| 2.20 | 1 | 1 | 1 | 1 |
| 2.22 | 1 | 1 | 1 | 1 |
| 2.23 | 7 | 1 | 9 | 5 |

Example B2

Postemergence herbicidal action

In a greenhouse, the following plants are grown in pots of 11 cm diameter until they have reached the 3–6-leaf stage, i.e. after about 2 weeks: soybeans, Avena fatua, Setaria, Lolium, Solanum, Stellaria, Sinapis and Phaseolus. They are then sprayed with an aqueous emulsion of wettable powder formulation of test compound at a concentration of 4 kg of active ingredient per hectare and subsequently kept for at 20°–24° C. and 45–60% relative humidity. The test is evaluated 15 days after treatment and the result is expressed using the same rating as in the preemergence test. The results are as follows:

TABLE 4

Postemergence action
Rate of application: 4 kg of active ingredient per hectare

| Compound | Avena | Setaria | Lolium | Solanum | Sinapis | Stellaria | Phaseolus |
|---|---|---|---|---|---|---|---|
| 1.1 | 1 | 1 | 2 | 1 | 1 | 1 | 2 |
| 1.2 | 1 | 1 | 1 | 1 | 1 | 1 | 2 |
| 1.3 | 1 | 4 | 2 | 1 | 1 | 1 | 1 |
| 1.4 | 1 | 3 | 1 | 1 | 1 | 1 | 3 |

TABLE 4-continued

Postemergence action
Rate of application: 4 kg of active ingredient per hectare

| Compound | Avena | Setaria | Lolium | Solanum | Sinapis | Stellaria | Phaseolus |
|---|---|---|---|---|---|---|---|
| 1.5 | 1 | 1 | 2 | 1 | 1 | 1 | 2 |
| 1.6 | 1 | 1 | 1 | 1 | 1 | 1 | 2 |
| 1.7 | 1 | 3 | 1 | 1 | 1 | 1 | 3 |
| 1.8 | 1 | 1 | 1 | 1 | 1 | 1 | 2 |
| 1.9 | 1 | 1 | 1 | 1 | 1 | 1 | 2 |
| 1.11 | 1 | 1 | 1 | 1 | 1 | 1 | 3 |
| 1.12 | 1 | 1 | 2 | 1 | 1 | 1 | 8 |
| 1.13 | 1 | 2 | 1 | 1 | 1 | 1 | 2 |
| 1.14 | 2 | 2 | 2 | 1 | 1 | 1 | 2 |
| 1.15 | 1 | 1 | 1 | 1 | 1 | 1 | 7 |
| 1.16 | 2 | 4 | 3 | 1 | 1 | 2 | 9 |
| 1.17 | 1 | 1 | 2 | 1 | 1 | 1 | 2 |
| 1.19 | 1 | 5 | 3 | 1 | 1 | 1 | 8 |
| 1.20 | 1 | 1 | 2 | 1 | 1 | 1 | 1 |
| 1.21 | 1 | 1 | 1 | 1 | 1 | 1 | 1 |
| 1.22 | 1 | 1 | 1 | 1 | 1 | 2 | 4 |
| 1.24 | 1 | 1 | 1 | 1 | 1 | 1 | 2 |
| 1.25 | 1 | 1 | 1 | 1 | 1 | 1 | 2 |
| 1.36 | 2 | 1 | 2 | 1 | 1 | 1 | 8 |
| 1.37 | 1 | 1 | 1 | 1 | 1 | 1 | 3 |
| 1.38 | 1 | 1 | 1 | 1 | 1 | 1 | 3 |
| 1.39 | 1 | 1 | 1 | 1 | 1 | 1 | 3 |
| 1.40 | 1 | 1 | 1 | 1 | 1 | 1 | 2 |
| 1.41 | 1 | 2 | 3 | 1 | 1 | 1 | 6 |
| 1.42 | 1 | 1 | 2 | 1 | 1 | 1 | 1 |
| 1.43 | 1 | 5 | 4 | 1 | 1 | 1 | 5 |
| 1.44 | 1 | 1 | 1 | 1 | 1 | 1 | 2 |
| 1.45 | 1 | 7 | 4 | 1 | 1 | 5 | 3 |
| 1.46 | 1 | 1 | 1 | 1 | 1 | 1 | 1 |
| 1.47 | 1 | 1 | 1 | 1 | 1 | 1 | 1 |
| 1.48 | 1 | 1 | 1 | 1 | 1 | 1 | 2 |
| 1.49 | 1 | 1 | 1 | 1 | 1 | 1 | 2 |
| 1.50 | 1 | 1 | 1 | 1 | 1 | 1 | 2 |
| 1.51 | 1 | 1 | 1 | 1 | 1 | 1 | 2 |
| 2.1 | 1 | 1 | 1 | 1 | 1 | 1 | 2 |
| 2.2 | 1 | 1 | 1 | 1 | 1 | 1 | 2 |
| 2.3 | 1 | 3 | 1 | 1 | 1 | 1 | 2 |
| 2.4 | 1 | 2 | 1 | 1 | 1 | 1 | 2 |
| 2.5 | 1 | 1 | 1 | 1 | 1 | 1 | 2 |
| 2.6 | 1 | 7 | 3 | 1 | 1 | 1 | 8 |
| 2.10 | 1 | 1 | 3 | 1 | 1 | 1 | 5 |
| 2.11 | 5 | 9 | 9 | 8 | 2 | 8 | 8 |
| 2.12 | 4 | 9 | 7 | 1 | 2 | 5 | 5 |
| 2.13 | 1 | 1 | 2 | 1 | 1 | 2 | 1 |
| 2.14 | 4 | 6 | 2 | 1 | 2 | 7 | 3 |
| 2.16 | 4 | 1 | 3 | 1 | 2 | 4 | 3 |
| 2.17 | 4 | 1 | 5 | 2 | 2 | 5 | 3 |
| 2.18 | 1 | 1 | 2 | 1 | 1 | 1 | 1 |
| 2.19 | 6 | 8 | 7 | 8 | 1 | 4 | 4 |
| 2.20 | 1 | 1 | 1 | 1 | 1 | 1 | 2 |
| 2.21 | 1 | 1 | 1 | 1 | 1 | 1 | 2 |
| 2.22 | 1 | 1 | 1 | 1 | 1 | 1 | 1 |
| 2.23 | 5 | 9 | 2 | 1 | 2 | 4 | 9 |

Example B3

Action as Rice Herbicides

The weeds Echinocloa crus galli and Monochoria vaginalis are sown in plastic beakers filled with soil (surface area 60 cm², volume 500 ml) and then the beakers are filled with water to the surface of the soil. Three days after sowing, further water is added until the water level is somewhat above the surface of the soil (3 to 5 mm). The test compounds formulated as aqueous emulsions are sprayed onto the surface of the water in a concentration corresponding to a field application rate of 4 kg/ha and to an amount of 550 l/ha. After the application, the beakers are kept in a greenhouse under optimum growth conditions for the weeds, i.e. at 25°–30° C. and high humidity. The tests are evaluated in accordance with the rate of growth and plant species 2–3 weeks after application. A linear rating of 1 to 9 is used for the evaluation, the criteria being as follows:

1 = plant has not germinated
2–4 = intermediate stages of damage
5 = average activity
6–8 = intermediate stages of damage
9 = no activity

TABLE 5

| Compound | Echinochloa c.g. | Monochoria vag. |
|---|---|---|
| 1.24 | 1 | 3 |
| 1.25 | 1 | 1 |
| 1.45 | 6 | 7 |
| 1.46 | 3 | 5 |
| 1.47 | 1 | 1 |
| 1.48 | 4 | 6 |
| 1.49 | 2 | 2 |
| 1.50 | 2 | 5 |
| 2.12 | 3 | 4 |
| 2.13 | 2 | 1 |
| 2.14 | 3 | 1 |

TABLE 5-continued

| Compound | Echinochloa c.g. | Monochoria vag. |
| --- | --- | --- |
| 2.15 | 5 | 3 |
| 2.16 | 3 | 1 |
| 2.17 | 3 | 1 |
| 2.18 | 1 | 1 |
| 2.19 | 2 | 2 |
| 2.20 | 1 | 1 |
| 2.21 | 1 | 2 |
| 2.22 | 1 | 1 |

Example B4

Action Against *Nilaparvata Lugens* (Nymphs)

The test is carried out with growing plants. The procedure is that 10 to 15 rice plants (20 days old; height about 15 cm) are planted into each of a number of pots having a diameter of about 5.5 cm. The plants in each pot are then sprayed on a rotary table with 40 ml of an acetonic solution containing 400 ppm of the test compound. After the spray coating has dried, each plant is populated with 20 nymphs of the species Nilaparvata lugens (in the second to third stage). To prevent the cicadas from escaping, a plexiglass cylinder is slipped over the populated plants and sealed with a gauze top. The test is carried out at 24°-28° C. and 55-65% relative humidity, and under 16 hours illumination. Evaluation of the percentage mortality is made after 6 days.

Compounds of the formulae I and III are very effective in this test. Thus, for example, compounds 1.51 and 2.6 effect 80-100% mortality.

Example B5

Action Against Soil Insects (*Diabrotica Balteata*)

Maize seedlings (1-3 cm) in a plastic beaker (volume 200 ml) which contains a round filter are treated dropwise with 1 ml of a solution containing 400 ppm of test compound and are then each populated with 10 Diabrotica balteata larvae. The test is carried out at 22°-26° C. and 40-60% relative humidity in daylight. Evaluation is made after 6 days. Compounds of formulae I and III are very effective in this test. For example, compounds 1.13 and 2.14 effect a mortality of over 80%.

Example B6

Systemic Insecticidal Action Against *Aphis Craccivora*

Pea seedlings which have been infested with aphids of the species Aphis craccivora 24 hours before the start of the test are briefly immersed in 20 ml of an aqueous mixture containing 400 ppm of test compound. The aqueous mixture is prepared from an emulsifiable concentrate or wettable powder formulation of the test compound. The plants are then put into a small glass (volume 20 ml) containing the test solution. The test is carried out at 19°-23° C. and 45-65% relative humidity in daylight. Evaluation is made after 3 and 5 days. Compounds of formulae I and III are very effective in this test. For example, compounds 1.10, 2.2 and 2.23 effect a mortality of over 80%.

What is claimed is:

1. A 4-methylamino-1,2,4-triazin-5-one of the formula

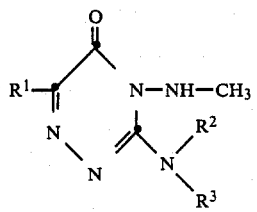

wherein
$R^1$ is phenyl, or phenyl substituted by one or more members selected from the group consisting of halogen, $C_1$-$C_4$alkyl, $C_1$-$C_4$haloalkyl, $C_1$-$C_4$alkoxy or $C_1$-$C_4$haloalkoxy,
$R^2$ is hydrogen or methyl, and
$R^3$ is cyclopropyl, cyclopropylmethyl, $C_1$-$C_4$alkyl, $C_3$-$C_4$alkenyl or $C_3$-$C_4$alkynyl.

2. A compound according to claim 1, wherein $R^2$ is hydrogen.

3. A compound according to claim 1, selected from 3,4-bis(methylamino)-6-phenyl-4H-1,2,4-triazin-5-one and
3,4-bis(methylamino)-6-(2-fluorophenyl)-4H-1,2,4-triazin-5-one.

* * * * *